United States Patent
Bonillas Vaca et al.

(10) Patent No.: US 12,310,665 B2
(45) Date of Patent: May 27, 2025

(54) SYSTEM AND METHOD FOR INTRA-OPERATIVE PERCUTANEOUS ABLATION PLANNING

(71) Applicant: Canon U.S.A., Inc., Melville, NY (US)

(72) Inventors: Antonio Bonillas Vaca, Boston, MA (US); Barret Daniels, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 987 days.

(21) Appl. No.: 17/351,698

(22) Filed: Jun. 18, 2021

(65) Prior Publication Data

US 2022/0039865 A1    Feb. 10, 2022

Related U.S. Application Data

(60) Provisional application No. 63/062,184, filed on Aug. 6, 2020.

(51) Int. Cl.
*A61B 34/10* (2016.01)
*A61B 18/14* (2006.01)
(Continued)

(52) U.S. Cl.
CPC ............... *A61B 34/10* (2016.02); *A61B 18/14* (2013.01); *A61B 34/30* (2016.02);
(Continued)

(58) Field of Classification Search
CPC ......... A61B 34/10; A61B 18/14; A61B 34/30; A61B 2018/00577; A61B 2018/00738;
(Continued)

(56) References Cited

U.S. PATENT DOCUMENTS 9,439,622 B2 *   9/2016   Case .................... A61B 34/20
9,782,147 B2 * 10/2017   Martin .................. A61B 34/20
(Continued)

FOREIGN PATENT DOCUMENTS

JP         2015529114 A      10/2015
WO      2019/010232 A1      1/2019

OTHER PUBLICATIONS

Villard, Caroline, Luc Soler, Afshin Gangi, Didier Mutter, and Jacques Marescaux. "Toward realistic radiofrequency ablation of hepatic tumors 3D simulation and planning." In Medical Imaging 2004: Visualization, Image-Guided Procedures, and Display, vol. 5367, pp. 586-595. SPIE, 2004. (Year: 2004).*

(Continued)

*Primary Examiner* — Juan C Ochoa
(74) *Attorney, Agent, or Firm* — Canon U.S.A., Inc. IP Division (57) ABSTRACT

Apparatus, systems, and methods for percutaneous ablation of a tumor in a sample, object, or subject, and more specifically, for percutaneous tumor ablation with the ability for real-time, intra-operative ablation planning, execution, and/or adjustment, are provided herein. One or more apparatuses, systems, and methods may operate to detect a region of interest in an image, subject to an ablation or radiotherapy process or an ablation or radiotherapy planning; identify a position of a needle in the image; calculate a trajectory and a depth of the needle based on an insertion information of the needle, and display the needle trajectory and the depth on the image.

23 Claims, 4 Drawing Sheets

(51) Int. Cl.
*A61B 34/30* (2016.01)
*A61B 18/00* (2006.01)

(52) U.S. Cl.
CPC .............. *A61B 2018/00577* (2013.01); *A61B 2018/00738* (2013.01); *A61B 2018/1425* (2013.01); *A61B 2034/107* (2016.02)

(58) Field of Classification Search
CPC ...... A61B 2018/1425; A61B 2034/107; A61B 18/1477; A61B 2018/143
USPC .......................................................... 703/2, 1
See application file for complete search history.

(56) References Cited

U.S. PATENT DOCUMENTS

| | | | | |
|---|---|---|---|---|
| 9,839,482 | B2 | 12/2017 | Mielekamp et al. | |
| 2013/0072784 | A1* | 3/2013 | Velusamy | A61B 18/02 600/424 |
| 2014/0073907 | A1* | 3/2014 | Kumar | A61B 10/0241 600/407 |
| 2014/0201669 | A1* | 7/2014 | Liu | A61B 34/10 715/771 |
| 2016/0335413 | A1* | 11/2016 | Davidson | G16H 50/50 |
| 2020/0008875 | A1 | 1/2020 | Lu | |

OTHER PUBLICATIONS

Berber, Eren. "The first clinical application of planning software for laparoscopic microwave thermosphere ablation of malignant liver tumours." Hpb 17, No. 7 (2015): 632-636. (Year: 2015).*

Tani, Soichiro, et al. "Three-dimensional quantitative assessment of ablation margins based on registration of pre-and post-procedural MRI and distance map." International journal of computer assisted radiology and surgery 11 (2016): 1133-1142. (Year: 2016).*

Ren, Hongliang, Enrique Campos-Nanez, Ziv Yaniv, Filip Banovac, Hernan Abeledo, Nobuhiko Hata, and Kevin Cleary. "Treatment planning and image guidance for radiofrequency ablation of large tumors." IEEE journal of biomedical and health informatics 18, No. 3 (2013): 920-928. (Year: 2013).*

Boctor, Emad M., Michael A. Choti, Everette C. Burdette, and Robert J. Webster Iii. "Three-dimensional ultrasound-guided robotic needle placement: an experimental evaluation." The International Journal of Medical Robotics and Computer Assisted Surgery 4, No. 2 (2008): 180-191. (Year: 2008).*

Tinguely, Pascale, Matteo Fusaglia, Jacob Freedman, Vanessa Banz, Stefan Weber, Daniel Candinas, and Henrik Nilsson. "Laparoscopic image-based navigation for microwave ablation of liver tumors—a multi-center study." Surgical endoscopy 31 (2017): 4315-4324. (Year: 2017).*

E. Ben-David, et al., Evaluation of a CT-Guided Robotic System for Precise Percutaneous Needle Insertion, Journal of Vascular and Interventional Radiology: JVIR, 2018, 7 pages.

* cited by examiner

SYSTEM AND METHOD FOR INTRA-OPERATIVE PERCUTANEOUS ABLATION PLANNING

CROSS REFERENCE TO RELATED PATENT APPLICATIONS

This application claims priority from U.S. Provisional Patent Application No. 63/062,184, filed on Aug. 6, 2020, in the United States Patent and Trademark Office, the disclosure of which is incorporated herein in its entirety by reference.

FIELD OF THE DISCLOSURE

The present disclosure relates generally to systems and methods percutaneous ablation. More particularly, the subject disclosure is directed to percutaneous tumor ablation with the ability for real-time, intra-operative ablation planning.

BACKGROUND OF THE DISCLOSURE

Image-guided percutaneous tumor ablation is a very popular alternative to surgical resection, and provides a minimally invasive option to eradicating solid tumors. Percutaneous ablations are performed by manually guiding ablation needle(s) to a lesion within the body utilizing medical imaging, such as CT, MRI, and/or Ultrasound, for iterative needle targeting feedback. Once the needle(s) reach the lesion, thermal ablation is performed to either heat or freeze the cancerous tissue to induce necrosis. The success of percutaneous ablation procedures hinges on the physicians ability to adequately visualize the lesion, accurately guide the ablation needle(s) to the lesion, and repeatedly achieve minimal ablation margins. Many of the targeting challenges are overcome by manual manipulation of the needle(s) and a stepwise iterative path-correction approach, but targeting a point within the body is only part of the treatment challenge.

The ability for the physician to plan and execute a needle trajectory that places the needle(s) in a position where an adequate ablation margin can be achieved, while reducing damage to healthy tissue, is the most daunting and difficult challenge.

As an indication of this inefficiency, recent studies have shown percutaneous ablation disease recurrence rates of 90% with 0 mm margins, and 5% recurrence with greater than 1 cm margins; thus illustrating the need for better ablation planning tools to help the physician repeatedly achieve minimum ablation margins and thus reduce recurrence rates.

The majority of physicians utilize standard diagnostic image viewing software to perform percutaneous ablations rather than a software package tailored for the procedure. The physician is forced to mentally map a manufacturer supplied ablation zone specification from a printed chart into the images and judge whether the ablation will provide adequate margins. Furthermore, the physician must mentally account for varying tissue characteristics which can have a large effect on the in-practice ablation size. The lack of ablation planning tools make performing percutaneous ablation procedures extremely difficult for physicians, and potentially dangerous for the patient.

Various examples in attempting to resolve this issue can be seen, for instance in U.S. Pat. No. 9,839,482, which describes segmenting a tumor and overlaying a planned needle trajectory and corresponding ablation zone for that needle. The patent discusses a safety margin around the tumor and the ability to visualize that, as well as methods to convey that parts of the lesion lie outside the planned ablation zone. However, the patent in limited in that there is no intra-operative ablation planning, no needle detection and planning based on needle detection, and no auto calculations of optimal position and size of ablation zone based on trajectory.

Another publication attempting to address the issue is "Evaluation of a CT-Guided Robotic System for Precise Percutaneous Needle Insertion." By j. Vasc Interv Radiol 2018. This paper describes a needle insertion using a novel robotic device, utilizing pre-planning of the needle trajectory and then selecting spots along that needle path in which the physician desires the robot to stop to check trajectory. However, the planning and marking stop points along the trajectory is all done during pre-operative planning. As such, there is no intra-operative ablation planning, and no projection of the needle trajectory along the path the needle is actually taking to adjust needle path.

Accordingly, there exists a need in the art for novel systems and methods for percutaneous ablation, wherein tumor ablation with real-time, intra-operative ablation planning is possible.

SUMMARY

Thus, to address such exemplary needs in the industry, the presently disclosed apparatus teaches an image processing apparatus for supporting an ablation or radiotherapy process or planning, comprising: a processor configured for intra-operative operation which: detects a region of interest in an image which is subject to an ablation or radiotherapy process or ablation or radiotherapy planning, then identifies the position of a needle in the image, and calculates a trajectory and depth of the needle based on an insertion information of the needle, all the while causing a display to display the needle trajectory and depth on the image, which allows an end user to set an ablation zone in the region of interest, and an ablation size in the region of interest; and allows the end user to adjust the needle trajectory and depth to reflect the ablation zone and ablation size set by the end user.

In further embodiments, the processor allows the end user to reset the ablation zone or ablation size, intra-operatively, and adjust the needle trajectory and depth to reflect the resetting.

In yet another embodiment, the needle may a multiple parallel needle for additional length.

It is further contemplated that the processor further operates to pre-segment a lesion in the ablation zone based on feedback from the end user. Additionally, the processor further operates to provide real-time feedback of a minimum ablation margin to the end user, and/or the processor further operates to provide real-time feedback of a maximum ablation margin to the end user.

It is further contemplated that the processor may provide real-time feedback of a percent coverage of a tumor, wherein the percent coverage of the tumor is derived from a minimum ablation margin and maximum ablation margin.

In yet another embodiment, the processor further operates to pre-segment a critical structure in the image based on feedback from the end user.

It is further envisioned that the needle is rotatable about an insertion point of a subject, wherein the rotatable needle can create an ablation zone about a center of the ablation.

In further embodiments, the apparatus may comprise a stereotactic device for guiding the needle in three dimensions.

Furthermore, needle insertion may be controlled by a robot.

Further embodiments contemplated include, an image processing apparatus for supporting an ablation or radiotherapy process or planning, comprising: a processor configured for intra-operative operation which: detects a region of interest in an image, subject to an ablation or radiotherapy process or ablation or radiotherapy planning; receives an input from an end user, including minimum ablation margin, maximum ablation margin, and percent tumor coverage; iterates a position of an ablation zone in the image; calculates a needle trajectory and depth of insertion of the needle based on the iterated position of the ablation zone; and causes a display to display the needle trajectory and depth of insertion on the image for insertion by the end user.

The subject disclosure further teaches a method for performing ablation planning and/or performance, the method comprising: providing an image processing apparatus, having a processor configured for intra-operative operation; identifying a region of interest in an image, subject to the ablation planning and/or performance; providing one or more input from an end user, including a minimum ablation margin, a maximum ablation margin, and a percent tumor coverage, to the image processing apparatus; iterating a position of an ablation zone in the image from the one or more input from the end user; calculating a needle trajectory and depth of insertion of the needle based on the iterated position of the ablation zone; and displaying the needle trajectory and depth of insertion on the image for insertion of the needle by the end user.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF THE DRAWINGS

Further objects, features and advantages of the present invention will become apparent from the following detailed description when taken in conjunction with the accompanying figures showing illustrative embodiments of the present invention.

Throughout the Figures, the same reference numerals and characters, unless otherwise stated, are used to denote like features, elements, components or portions of the illustrated embodiments. In addition, reference numeral(s) including by the designation "'" (e.g. 12' or 24') signify secondary elements and/or references of the same nature and/or kind. Moreover, while the subject disclosure will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION OF THE DISCLOSURE

Figure 1:
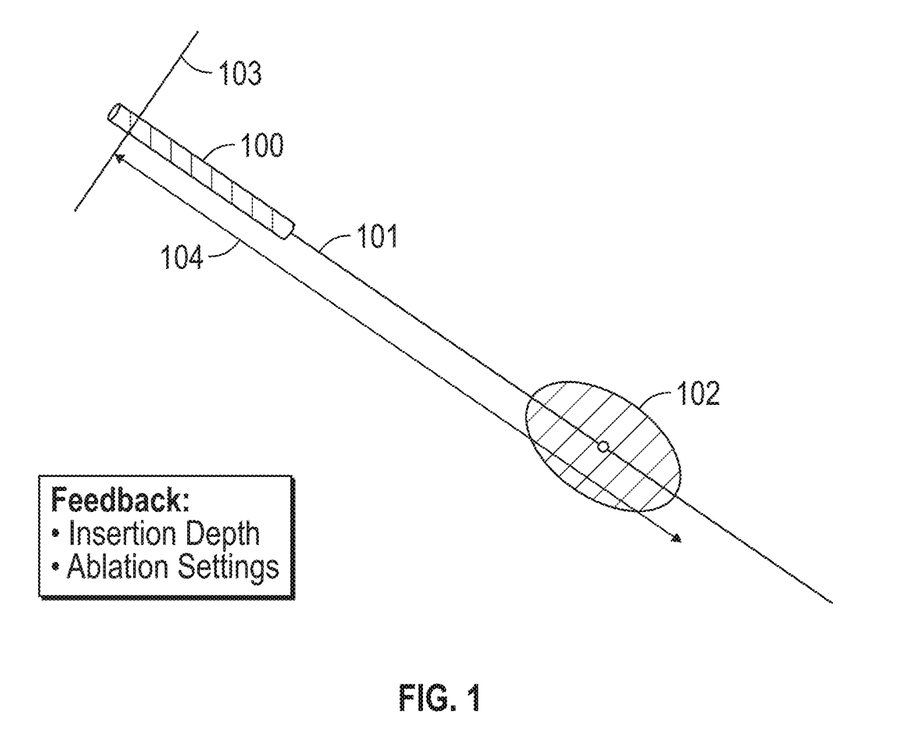
FIG. 1 is an image of an exemplary needle projection path, according to one or more embodiment of the subject apparatus, method or system.

FIG. 1 is an image of an exemplary needle projection path, according to one or more embodiment of the subject apparatus, method or system. In this embodiment, the subject method uses a standard line detection algorithm such as the Hough Transform to detect the position of the needle 100 in the acquired CT images. A parallel line from the existing detected needle is used as a projection of that line 101 beyond the needle tip, providing the trajectory of the needle. The physician or technologist can adjust the ablation zone 102 settings and thus ablation size in the software to visualize the corresponding ablation zone 102. The physician can drag the ablation zone up and down with respect to the projected needle path 101 and the software provides feedback to the physician as to the insertion depth distance 104 from skin surface 103 needed to reach that ablation zone 102. If a single needle cannot reach the desired ablation zone 102, then the physician can select a multiple parallel needle configuration and visualize the addition of a second or third needle providing a large enough ablation zone 102 to encompass the lesion.

Figure 2:
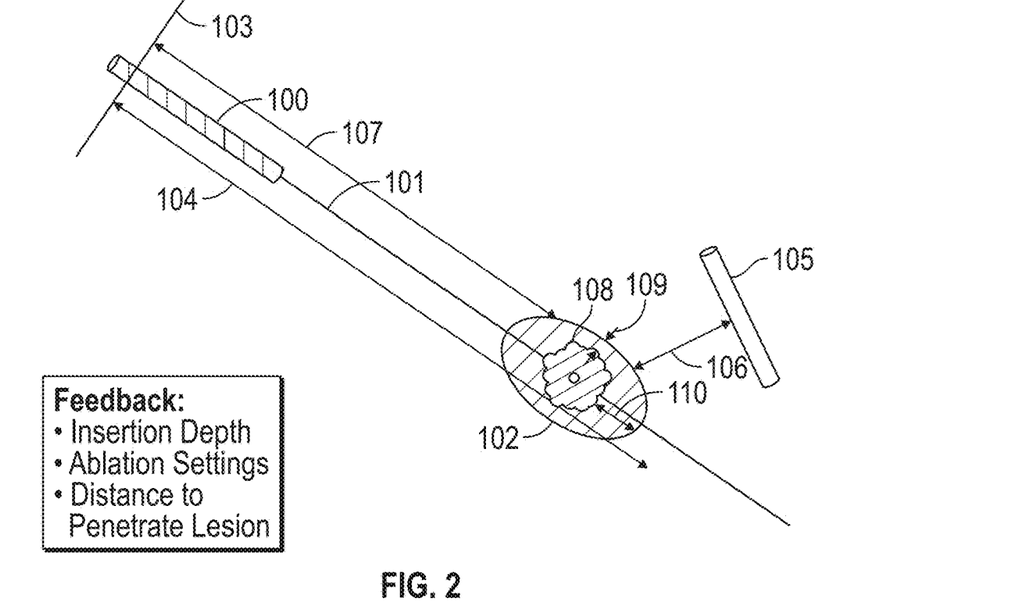
FIG. 2 depicts a perspective view of an exemplary needle projection path, according to one or more embodiment of the subject apparatus, method or system.

FIG. 2 depicts a perspective view of an exemplary needle projection path, according to one or more embodiment of the subject apparatus, method or system.

FIG. 2 incorporates various features of the embodiment provided in FIG. 1, however, the targeted lesion is pre segmented 108 by the physician. The physician can then drag and adjust the ablation zone 102 and realize real time feedback on the minimum ablation margin 109, maximum ablation margin 110, and amount of coverage of tumor (by percentage). The minimum ablation margin 109 is defined as the minimum distance between the edge of the tumor and the edge of the ablation zone 102. Maximum ablation margin 110 is defined as the maximum distance between the edge of the tumor 108 and the edge of the ablation zone 102. Percent tumor coverage is defined as the percentage of the segmented tumor which is covered by the ablation zone 102. In an extension of this embodiment, the physician or technologist will pre-segment a critical structure 105 to avoid, such as a blood vessel, and the software will provide the minimum feedback distance between that critical structure and the edge of the ablation zone 106. The software will then provide the insertion depth distance 104 from the skin surface 103, needed for successful ablation. The software will also provide the insertion distance from the skin surface to penetrate the lesion 107.

Figure 3:
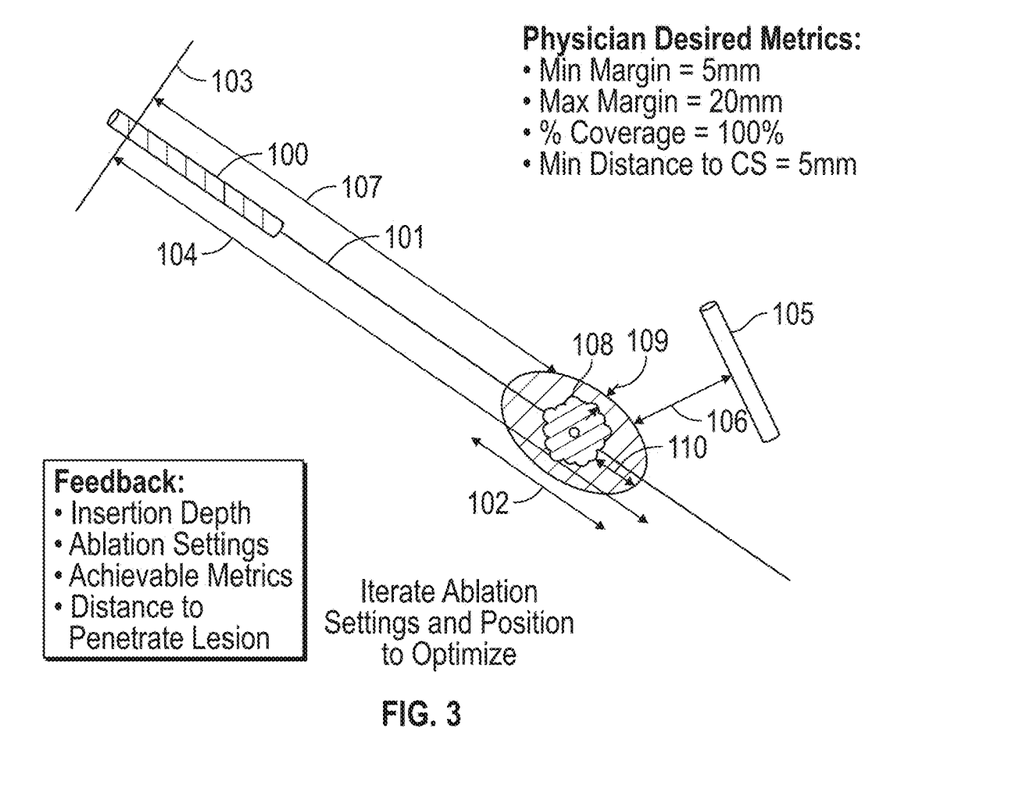
FIG. 3 provides an exemplary needle projection path, according to one or more embodiment of the subject apparatus, method or system.

In FIG. 3 the various features provided in FIGS. 1 and 2 are present, and further augmented by the physician's inputting their desired metrics for minimum 109 and maximum ablation margin 110, percent tumor coverage, and minimum distance to critical structures. The software will then iterate the position of the ablation zone 102 on the projected needle trajectory 101 and test each ablation size in those positions to find the position and setting of the ablation zone 102 that achieves the metrics requested by the physician. If the single needle ablation zone sizes are insufficient to achieve the physician's metrics, then the software can add a second and third needle to determine if the metrics are achievable with that configuration. This embodiment allows the physician to very quickly continue with needle insertion, with confidence that the desired metrics will be achieved, or manipulate the trajectory and take another scan until it can be achieved. By having the software rapidly iterate, the physician saves time, the patient received less radiation dose as less CT scans are needed to perform the procedure, and the patient is under anesthesia for a shorter period of time.

Figure 4:
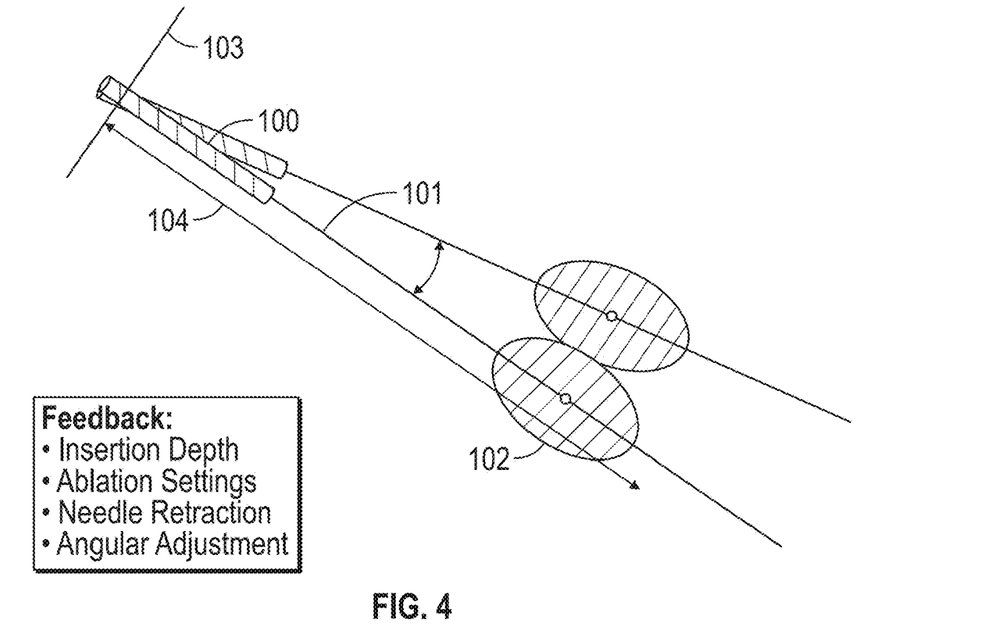
FIG. 4 is an image of an exemplary rotatable needle projection paths, according to one or more embodiment of the subject apparatus, method or system.

In FIG. 4 we introduce the ability to manipulate the projected needle path 101 so that it rotates around the point where the needle 100 intersects the skin surface 103. A maximum allowed linear displacement of the center of the ablation zone 102 can be defined, based on user input or calculated from tissue characteristics derived from image intensity values. Using two different anatomical planes for rotation (e.g. left-right and cranial-caudal) allows for adjusting the path three-dimensionally. Feedback can be provided to the end user with the required adjustment angles and the length of needle retraction necessary to remain within the displacement limits. This added ability to project the needle path in two-dimensions allows for better coverage of the target area, further eliminating any errors and increasing accuracy.

In further embodiments, the rotatable needle 100 projection path detailed above can include pre segmented 108 of the lesion/target by the physician. The physician can then drag and adjust the ablation zone 102 and get real time feedback on the minimum ablation margin 109, maximum ablation margin 110, and percent coverage of the tumor. In an extension of this embodiment, the physician or technologist will pre-segment a critical structure 105 such as a blood vessel to avoid and the software will feedback the minimum distance between that critical structure and the edge of the ablation zone 106. The software will then feedback to the physician the insertion depth distance 104 from skin surface 103 needed to achieve that ablation. The software will also provide the insertion distance from skin surface to penetrate the lesion 107.

In further embodiment, the physician can input a desired metrics for minimum and maximum ablation margin, percent tumor coverage, and minimum distance to critical structures. This embodiment allows the physician to very quickly continue with needle insertion with confidence the desired metrics will be achieved, or manipulate the trajectory and take another scan until it can be achieved, and may add automatic calculation of orientation adjustment angles needed to achieve the desired metrics.

Figure 5:
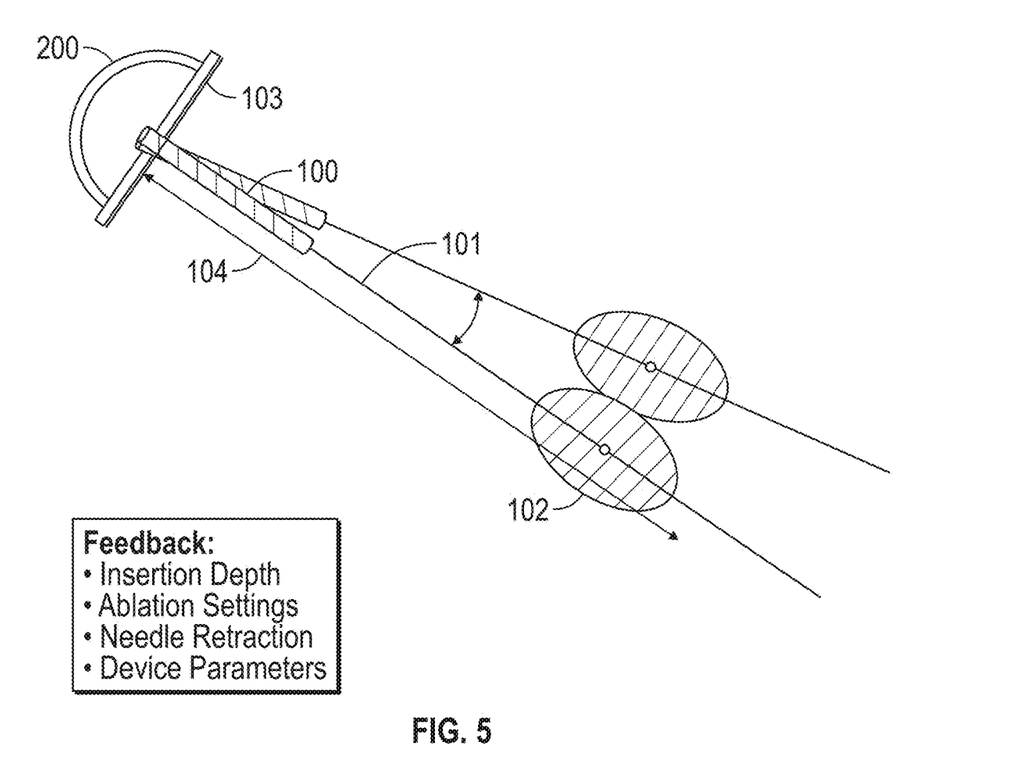
FIG. 5 depicts a perspective view of a rotatable needle projection paths, according to one or more embodiment of the subject apparatus, method or system.

The embodiment seen in FIG. 5 may teach the use of a stereotactic device 200, which can precisely guide a needle 100 in three-dimensional space, placed at or near the skin surface 103. The stereotactic device 200, depending on its mechanical design, has defined mechanical degrees of freedom and corresponding parameters to orient the needle in its three-dimensional frame of reference, and can be registered to the imaging frame of reference. The adjustment angles in image space can be translated to provide feedback on the corresponding device parameters.

Furthermore, lesion segmentation and ablation coverage metrics, and critical structure segmentation and avoidance metrics may be added to the stereotactic device 200 embodiment. Yet again, desired ablation coverage and critical structure avoidance metrics input, and automatic calculation of depth adjustment and ablation settings may be added, and automatic calculation of orientation adjustment angles and corresponding device parameters needed to achieve desired metrics may also be implemented to further streamline the process.

Figure 6:
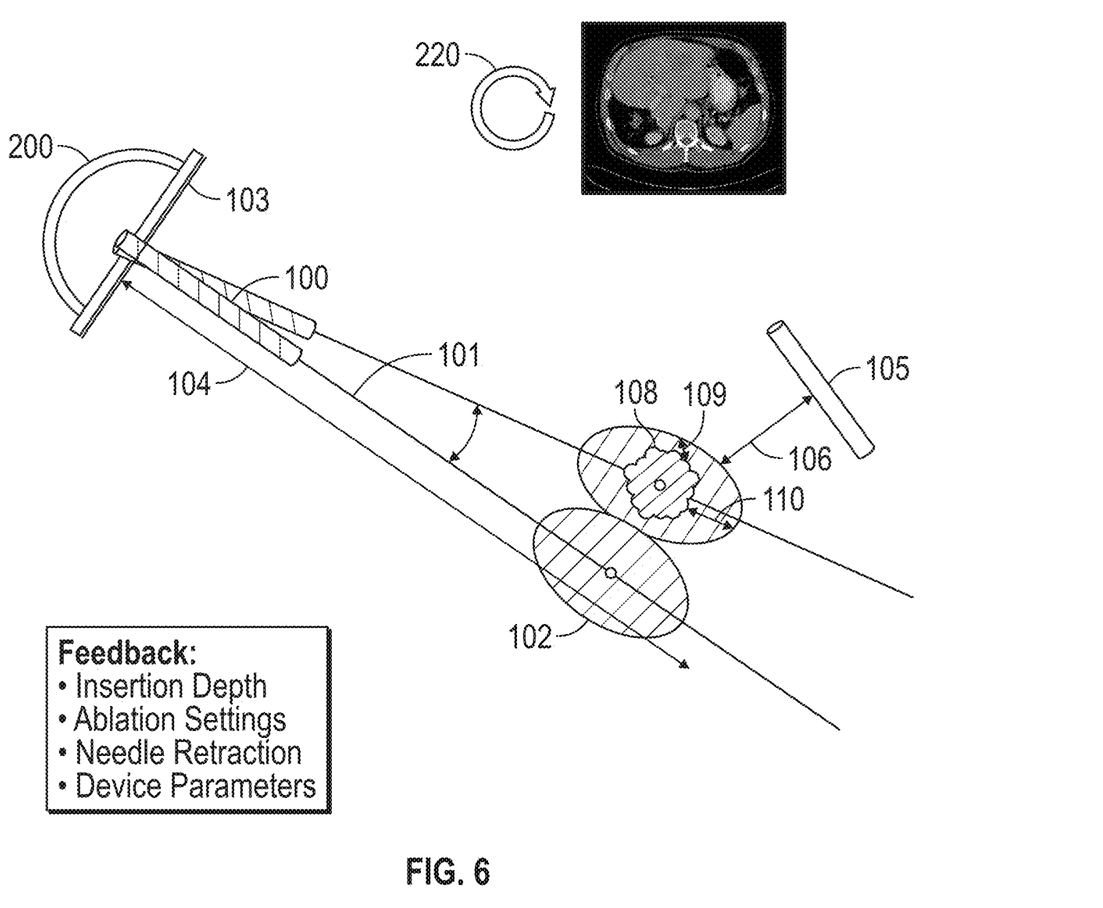
FIG. 6 provides exemplary needle projection paths of a rotatable needle, according to one or more embodiment of the subject apparatus, method or system.

Finally, the stereotactic device 200 and needle insertion can be robotically controlled, providing real-time imaging data input 220 (see FIG. 6) and re-segmentation. The insertion and adjustment of the stereotactic device 200 parameters can then be controlled automatically.

The invention claimed is:

1. An image processing apparatus for supporting an ablation or radiotherapy process or an ablation or radiotherapy intra-operative planning, comprising:
  a processor that operates, for intra-operative operation, to:
    detect a region of interest in an image of a target in a sample, object, or subject, the target being subject to an ablation or radiotherapy process or an ablation or radiotherapy intra-operative planning, the detected region of interest being disposed in or on the sample, object, or subject and including the target, and the image being taken intra-operatively and/or in real-time;
    identify a position of a needle in the image in relation to the target and/or to the sample, object, or subject;
    calculate a trajectory and a depth of the needle based on an insertion information of the needle, the trajectory extending from the needle to or through the target, and the depth being an insertion distance of the needle from a surface of the sample, object, or subject to the target;
    cause a display to display the trajectory and the depth of the needle on the image;
    allow an ablation zone to be set in the region of interest intra-operatively, and allow an ablation size to be set in the region of interest intra-operatively; and
    adjust the trajectory and the depth of the needle intra-operatively to reflect the ablation zone and the ablation size.

2. The apparatus of claim 1, wherein the processor further operates to one or more of the following:
  (i) allow the ablation zone and the ablation size to be set, intra-operatively, by an end user of the apparatus;
  (ii) allow the ablation zone and/or the ablation size to be reset, intra-operatively, and adjust the trajectory and the depth of the needle to reflect the resetting;
  (iii) allow an end user of the apparatus to reset the ablation zone and/or the ablation size, intra-operatively, and adjust the trajectory and the depth of the needle to reflect the resetting; and/or
  (iv) in a case where the image is taken in real time the image is taken in less than one or more of the following 1 second, 2 seconds, 3 seconds, 5 seconds, or 10 seconds.

3. The apparatus of claim 1, wherein the needle is a multiple parallel needle.

4. The apparatus of claim 1, wherein the processor further operates to one or more of the following:
  pre-segment the target or a lesion of the target in the ablation zone based on feedback or input, or pre-segment the target or a lesion of the target in the ablation zone based on feedback or input from an end user of the apparatus; and/or
  calculate or provide an additional insertion distance of the needle from a surface of the sample, object, or subject to a lesion of the target.

5. The apparatus of claim 1, wherein the processor further operates to: (i) provide real-time feedback of a minimum ablation margin to a display of or in communication with the apparatus and/or to an end user of the apparatus, or (ii) provide the real-time feedback of the minimum ablation margin to the display of or in communication with the apparatus and/or to the end user of the apparatus, wherein the real-time feedback is feedback that occurs in less than one or more of the following: 1 second, 2 seconds, 3 seconds, 5 seconds, or 10 seconds.

6. The apparatus of claim 1, wherein the processor further operates to: (i) provide real-time feedback of a maximum ablation margin to a display of or in communication with the apparatus and/or to an end user of the apparatus, or (ii) provide the real-time feedback of the maximum ablation margin to the display of or in communication with the apparatus and/or to the end user of the apparatus, wherein the real-time feedback is feedback that occurs in less than one or more of the following: 1 second, 2 seconds, 3 seconds, 5 seconds, or 10 seconds.

7. The apparatus of claim 1, wherein the processor further operates to one or more of the following:
   (i) provide real-time feedback of a percent coverage of the target or of a tumor in or of the target to a display of or in communication with the apparatus and/or to an end user of the apparatus, or provide the real-time feedback of the percent coverage of the target or of the tumor in or of the target to the display of or in communication with the apparatus and/or to the end user of the apparatus, wherein the real-time feedback is feedback that occurs in less than one or more of the following: 1 second, 2 seconds, 3 seconds, 5 seconds, or 10 seconds; and/or
   (ii) calculate or provide an additional insertion distance of the needle from a surface of the sample, object, or subject to a tumor in or of the target.

8. The apparatus of claim 7, wherein the percent coverage of the target or of the tumor is derived from a minimum ablation margin and a maximum ablation margin.

9. The apparatus of claim 1, wherein the processor further operates to: pre-segment a critical structure and/or a blood vessel in the image based on feedback or input, or pre-segment a critical structure and/or a blood vessel in the image based on feedback or input from an end user of the apparatus.

10. The apparatus of claim 1, wherein the needle is rotatable about an insertion point of the sample, object, or subject.

11. The apparatus of claim 10, wherein the rotatable needle creates the ablation zone about a center of the ablation.

12. The apparatus of claim 10, further comprising a stereotactic device for guiding the needle in three dimensions.

13. The apparatus of claim 1, wherein the needle insertion is controlled by a robot.

14. An image processing apparatus for supporting an ablation or radiotherapy process or an ablation or radiotherapy intra-operative planning, the image processing apparatus comprising:
   a processor that operates, for intra-operative operation, to:
      detect a region of interest in an image of a target in a sample, object, or subject, the target being subject to an ablation or radiotherapy process or an ablation or radiotherapy intra-operative planning, the detected region of interest being disposed in or on the sample, object, or subject and including the target, and the image being taken intra-operatively and/or in real-time;
      receive an input, the input including a minimum ablation margin, a maximum ablation margin, and a percent tumor coverage;
      identify a position of an ablation zone in the image in relation to the target and/or to the sample, object, or subject;
      calculate a needle trajectory and a depth of insertion of the needle based on the identified position of the ablation zone, the needle trajectory extending from the needle to or through the target, and the depth of insertion being an insertion distance of the needle from a surface of the sample, object, or subject to the target; and
      cause a display to display the needle trajectory and the depth of insertion on the image for insertion of the needle.

15. The apparatus of claim 14, wherein the processor further operates to one or more of the following:
   (i) allow the ablation zone and an ablation size to be set, intra-operatively, by an end user of the apparatus;
   (ii) allow the ablation zone and/or an ablation size to be reset, intra-operatively, and adjust the needle trajectory and the depth of the needle to reflect the resetting;
   (iii) allow an end user of the apparatus to reset the ablation zone and/or an ablation size, intra-operatively, and adjust the needle trajectory and the depth of the needle to reflect the resetting; and/or
   (iv) in a case where the image is taken in real time the image is taken in less than one or more of the following: 1 second, 2 seconds, 3 seconds, 5 seconds, or 10 seconds.

16. The apparatus of claim 14, wherein the needle is a multiple parallel needle.

17. The apparatus of claim 14, wherein the processor further operates to one or more of the following:
   pre-segment the target or a lesion of the target in the ablation zone based on feedback or input, or pre-segment the target or a lesion of the target in the ablation zone based on feedback or input from an end user of the apparatus; and/or
   calculate or provide an additional insertion distance of the needle from a surface of the sample, object, or subject to a lesion of the target.

18. The apparatus of claim 14, wherein the processor further operates to: (i) provide real-time feedback of a minimum ablation margin to a display of or in communication with the apparatus and/or to an end user of the apparatus, or (ii) provide the real-time feedback of the minimum ablation margin to the display of or in communication with the apparatus and/or to the end user of the apparatus, wherein the real-time feedback is feedback that occurs in less than one or more of the following: 1 second, 2 seconds, 3 seconds, 5 seconds, or 10 seconds.

19. The apparatus of claim 14, wherein the processor further operates to: (i) provide real-time feedback of a maximum ablation margin to a display of or in communication with the apparatus and/or to an end user of the apparatus, or (ii) provide the real-time feedback of the maximum ablation margin to the display of or in communication with the apparatus and/or to the end user of the apparatus, wherein the real-time feedback is feedback that occurs in less than one or more of the following: 1 second, 2 seconds, 3 seconds, 5 seconds, or 10 seconds.

20. The apparatus of claim 14, wherein the processor further operates to one or more of the following:
   (i) provide real-time feedback of a percent coverage of the target or of a tumor in or of the target to a display of or in communication with the apparatus and/or to an end user of the apparatus, or provide the real-time feedback of the percent coverage of the target or of the tumor in or of the target to the display of or in communication with the apparatus and/or to the end user of the apparatus, wherein the real-time feedback is feedback that occurs in less than one or more of the following: 1 second, 2 seconds, 3 seconds, 5 seconds, or 10 seconds; and/or (ii) calculate or provide an additional insertion distance of the needle from a surface of the sample, object, or subject to a tumor in or of the target.

21. The apparatus of claim 20, wherein the percent coverage of the target or of the tumor is derived from a minimum ablation margin and a maximum ablation margin.

22. The apparatus of claim 14, wherein the processor further operates to pre-segment a critical structure and/or a blood vessel in the image based on feedback or input, or pre-segment a critical structure and/or a blood vessel in the image based on feedback or input from an end user of the apparatus.

23. A method for performing an ablation or radiotherapy intra-operative planning and/or for performing an ablation or radiotherapy process using an image processing apparatus having a processor that operates to perform one or more intra-operative operations, the method comprising:

detecting or identifying a region of interest in an image of a target in a sample, object, or subject, the target being subject to the ablation or radiotherapy process or the ablation or radiotherapy intra-operative planning, the detected or identified region of interest being disposed in or on the sample, object, or subject and including the target, and the image being taken intra-operatively and/or in real-time;

receiving, via the image processing apparatus, or providing one or more inputs to the image processing apparatus, the one or more inputs including a minimum ablation margin, a maximum ablation margin, and a percent tumor coverage;

identifying a position of an ablation zone in the image in relation to the target and/or to the sample, object, or subject from the one or more inputs;

calculating a needle trajectory and a depth of insertion of the needle based on the identified position of the ablation zone, the needle trajectory extending from the needle to or through the target, and the depth of insertion being an insertion distance of the needle from a surface of the sample, object, or subject to the target; and displaying the needle trajectory and the depth of insertion on the image for insertion of the needle.

* * * * *